US008795358B2

(12) United States Patent
Michel et al.

(10) Patent No.: US 8,795,358 B2
(45) Date of Patent: Aug. 5, 2014

(54) ACCOMMODATIVE OCULAR IMPLANT

(75) Inventors: Francois Michel, Thonon les Balns (FR); Jean-Marc Buisine, Louvil (FR)

(73) Assignees: Centre National de la Recherche Scientifique—CNRS, Paris (FR); Francois Michel, Thonon-les-Bains (FR)

( * ) Notice: Subject to any disclaimer, the term of this patent is extended or adjusted under 35 U.S.C. 154(b) by 205 days.

(21) Appl. No.: 12/529,243

(22) PCT Filed: Feb. 8, 2008

(86) PCT No.: PCT/FR2008/000160
§ 371 (c)(1),
(2), (4) Date: Dec. 2, 2009

(87) PCT Pub. No.: WO2008/119894
PCT Pub. Date: Oct. 9, 2008

(65) Prior Publication Data
US 2010/0121443 A1 May 13, 2010

(30) Foreign Application Priority Data
Mar. 1, 2007 (FR) ...................................... 07 53575

(51) Int. Cl.
*A61F 2/16* (2006.01)
(52) U.S. Cl.
USPC .................................. 623/6.22; 623/6.37
(58) Field of Classification Search
None
See application file for complete search history.

(56) References Cited

U.S. PATENT DOCUMENTS

| 4,373,218 | A | * | 2/1983 | Schachar | 623/6.13 |
|---|---|---|---|---|---|
| 5,712,721 | A | * | 1/1998 | Large | 359/245 |
| 6,733,122 | B1 | * | 5/2004 | Feurer et al. | 351/160 R |
| 2003/0018383 | A1 | * | 1/2003 | Azar | 623/6.22 |
| 2006/0136055 | A1 | | 6/2006 | Michel | |

FOREIGN PATENT DOCUMENTS

| FR | 2 777 091 A1 | 10/1999 |
|---|---|---|
| WO | WO 85/05466 A | 12/1985 |
| WO | WO 94/23334 A | 10/1994 |
| WO | WO 03/007851 A | 1/2003 |

* cited by examiner

*Primary Examiner* — David H Willse
*Assistant Examiner* — Tiffany Shipmon
(74) *Attorney, Agent, or Firm* — Arent Fox LLP

(57) ABSTRACT

The invention relates to a device (1) for the vision correction of an eye (6), comprising: a converter (3, 3A, 3B, 5A, 5B) which can generate an electrical and/or magnetic and/or electromagnetic signal in response to the mechanical energy generated by a movement of the eye; and a soft lens (2) intended to be aligned with the eye. The converter is positioned in relation to the lens such that the electrical and/or magnetic and/or electromagnetic signal generated during the movement of the eye causes the optical properties of the lens to change. The invention is characterised in that the lens (2) includes a polymer material (7) containing a material (4) having a refractive index that can vary under the action of the electrical and/or magnetic and/or electromagnetic signal generated during a movement of the eye.

19 Claims, 5 Drawing Sheets d)

a)

b)

c)

¹

ACCOMMODATIVE OCULAR IMPLANT

The invention relates to a device for the vision correction of an eye including:

a converter which can generate an electrical and/or magnetic and/or electromagnetic signal in response to the mechanical energy generated by a movement of the eye;

a soft lens arranged so as to be aligned with the eye, the converter being positioned in relation to the lens such that the electrical and/or magnetic and/or electromagnetic generated during the movement of the eye causes the optical properties of the lens to change.

For a converter capable of generating an electrical signal, such a device is described in the international application WO 2004/004605. This document relates to a device of the ocular implant type wherein the soft lens is an intraocular lens which can be implanted in the patient's eye, for example when the patient suffers from cataract. In this document, a converter makes it possible to transform the mechanical energy which is generated by the movement of an eye into an electrical signal. This converter more particularly includes pressure sensors which detect the convergence movement of the eyes. This electrical signal is then supplied to the lens in the form of a detector voltage. Under the effect of such electrical voltage, the radius of curvature of the length undergoes a modification because of the piezoelectric effect. This modification is caused by a open loop wire movable under the effect of an electrical voltage which surrounds the lens and thus modifies the radius of curvature thereof when a voltage is applied. Such a device is pseudo-accommodative in the meaning that accommodation is carried out as a reaction to the movement of both eyes, when the eyes converge upon the passage from a far vision to a near vision. The effect of the modification of the curvature is then performed when this convergence condition is detected.

In the above-mentioned application, the movement generating a modification of the optical properties of the lens is a particular movement of both eyes corresponding to a convergence. However, within the scope of the invention, the movement of the eye can be any movement, for example defined by a variation in the orientation in space of the optical axis of an eye. Particular properties of elements of the invention can then be defined as a function of a particular movement. Such a device has the important advantage that the mechanical energy related to the movement of the eyes is transformed into an electrical energy liable to be used for modifying the optical properties of the lens through a piezoelectric effect. Using mechanical energy as a source of initial energy more particularly in the form of a pressure, or of a variation in length or of a deformation has the advantage of not being related to the user's age. As a matter of fact, whatever his or her age, the movement of the eye is the same to converge.

Although it is advantageous for generating a pseudo-accommodative implant for the vision correction, such a device however has some disadvantages.

More particularly, it is difficult to modify the curvature of an intra-ocular lens since the latter is polluted by fibrotic deposits. The lens thus sticks to the fabrics on which it is placed which makes it impossible to modify the curvature in a controlled and satisfactory way reproducible over time.

In addition, in the above-mentioned international application, the structure and the composition of the lens are adapted so that the curvature can be modified as a response to the movement of the eyes. This composition is then no longer adapted for other types of modification of the optical properties of the lens.

In addition, it is known that, within the scope of an intra-ocular lens, the best way to insert the lens is to fold it, to insert it into a small size cut in the eye and to let the lens go back to a desired shape. Because of the means used for modifying the curvature in the above-mentioned international application, such a procedure is more complex.

The invention more particularly aims at remedying such drawbacks.

A problem solved by the invention thus consists in providing a device for the vision correction such as previously described, which can react to the mechanical energy generated by a movement of the eye and for which the modifications in the optical properties of the lens are simplified and better controlled. It is also suitable that the properties of the lens are stable in the absence of all electrical and/or magnetic and/or electromagnetic signals.

Document WO-A-03/007851 is also known, which discloses a device such as mentioned above.

In this document, liquid crystals are inserted into a bag to form the soft lens. Under the action of a contraction of the iris, the orientation of the liquid crystals can be modified so that the optical properties of the lens change.

However, the nature of the bag or the lens is not mentioned in this document.

Now, as mentioned above, within the scope of an intra-ocular lens, the best way to insert the lens consists in folding it, and inserting it into a small size cut in the eye and to let the lens go back to a desired shape. Now, if any bag including liquid crystals was used, this folding would cause a modification in the molecular arrangement of the liquid crystals. This modification can then be irreversible thus making the device unserviceable.

Further to the above-mentioned document, the invention thus aims at improving the soft lens.

Such problems are solved by a device for the vision correction of an eye such as previously described and characterised in that the soft lens includes a polymer material in which a material having a refraction index liable to vary under the action of the electrical and/or magnetic and/or electromagnetic signal in response to the movement of the eye is included.

Thanks to such a device, during the movements of the eye, the refraction index of the material can vary simply under the action of the electrical and/or magnetic and/or electromagnetic signal which modifies the optical properties of the lens. The device is thus liable to adapt in reaction to the movements of the eye. The insertion of the material having a variable refraction index into the polymer makes it possible to obtain this modification in an adapted way in response to a movement of the eye. As a matter of fact, it is possible to obtain some stability of the material having a variable index in the polymer in the absence of the electrical and/or magnetic and/or electromagnetic signal, while having a correct reactivity of the material to the signal applied in case of a movement of the eye.

According to the invention, the curvature of the lens is not necessarily modified, which makes it possible to avoid the above-mentioned problems related to the fibrosis of the fabrics in contact with the lens. The fact that the material having a variable refraction index is in the lens enables a simple control of the properties of modifying the lens, since the outside environment of the lens, such as the fibroses, does not influence the modification in the optical properties.

In the field of intra-ocular lens with a variable optical power, the American patient U.S. Pat. No. 4,373,218 is also known. Such patent teaches a device for the vision correction of an eye including a lens, the lens including liquid crystals.

Such liquid crystals have the known property of orientating under the effect of an electrical or magnetic or electromagnetic field. In the above-mentioned patent, according to one embodiment, electrodes are placed in the user's eye thus making it possible to detect an accommodation. However, in this patent, it is not the mechanical energy related to the movement of the eyes which is detected but an electrical potential generated by the muscles during the accommodation. The utilisation of the energy generated by the muscles during the accommodation is not sufficient since it is not stable and more particularly varies with the user's age, which will thus require a regular modification of the device. In addition, in the above-mentioned patent, the embodiment only uses the effect of an electrical field. However, within the scope of the invention, the used effects can be electrical and/or magnetic and/or electromagnetic.

In addition, the liquid crystals described in the above-mentioned patent are not adapted to react satisfactorily in response to a movement of the eye. As a matter of fact, they are not soaking in a medium allowing both a good orientation stability and a correct homogeneity in space and time in the absence of an electromagnetic field, and a correct spatial reaction and a correct homogeneity in presence of an electrical field. On the contrary, in the invention, positioning the material having a variable index in a polymer material makes it possible to gain this advantage. In addition, the invention makes it possible to gain this advantage in the presence of electrical and/or magnetic and/or electromagnetic fields.

In this patent, this is not the mechanical energy related to the movement of an eye which generates the electrical signal required for modifying the optical properties of the liquid crystals. This patent thus uses no converter. Because of the utilisation of the electrical potentials only generated by the muscle zones of the eyes, the device described in this patent is thus not satisfactory in practice.

The above-mentioned patent thus does not solve the above-mentioned problem related to the required modification as a reaction to a movement of the eye.

In addition, in the above-mentioned patent, it is difficult to give a desired shape to the lens. On the contrary, using a polymer material which can be used as a matrix makes it possible to impart such a shape in a simple way, more particularly through the construction of composite plates to be cut and to be machined. In addition, according to the invention, it is possible to provide a pre-defined orientation to the liquid crystals as soon as the lens is manufactured and not only when the lens is placed in the eye. Eventually, the lens according to the invention makes it possible, thanks to the utilisation of a polymer matrix including the material having a variable index, for example in the form of liquid crystals, to keep a satisfactory orientation of the liquid crystals even though the lens must be folded or handled prior to being introduced into the user's eye.

The application for a patent EP-A-1 068 555 is also known, wherein a device is described for the vision correction of an eye including a lens, including liquid crystals. Liquid crystals have the known property of orientating under the effect of a stress field. In this application, the material used for manufacturing the lens includes a three-dimension liquid crystal polymer. Now, in such a liquid crystal polymer, the crystalline liquid parts of the molecules are strictly frozen, so that the orientation effect of the crystalline liquid parts is obtained only when a high stress is exerted on the whole polymer. This is the reason why, in the present application, the modification or the orientation is provided under the action of a mechanical stress, for example during a blinking of the eyelid. Liquid crystal polymers described in the present application are thus not liable to orientate under the action of an electrical and/or magnetic and/or electromagnetic signal and more particularly they are not liable to orientate under the action of the electrical and/or magnetic and/or electromagnetic signal generated by the movement of the eye.

Now, other advantageous characteristics of the invention will be described.

When the signal generated by the converter following the movement of the eye is electrical, it can correspond to the relatively low voltage, typically of the order of 1 volt to 5, volts. Thus, it is advantageous that the effect of the reaction to the movement of the eye occurs even when the voltage generated by the movement of the eye is low. Only low voltages are compatible with the human body.

This additional advantage is reached according to one embodiment of the invention through the characteristic according to which the material includes liquid crystals having an orientation liable to vary under the action of an electrical and/or magnetic and/or electromagnetic signal during the movement of the eye.

According to this embodiment, further to the movement of the eye, the mechanical signal may generate an electrical and/or magnetic and/or electromagnetic signal and the liquid crystals orientate under the action of the electrical and/or magnetic and/or electromagnetic fields associated thereto, which results in the modification in the refraction index of the lens. The lens thus behaves like a birefringent material which reacts to the movements of the eye.

In addition, the liquid crystals have the property of easily orientating under the action of an even low electrical voltage, typically of the order of one volt. For applications to an intra-ocular implant, such a device thus makes it possible to use the low voltages generated by the movement of the eye.

Advantageously, the lens includes a composite of the polymer material and the liquid crystals. Thanks to this composite, the lens can be easily handled without irreversibly modifying the molecular arrangement of the liquid crystals which would make the device unserviceable.

According to one embodiment, the composite is a polymer matrix swollen with liquid crystals. Such an embodiment has the advantage of being easily produced. A polymer protection envelope can also be added which is aimed at protecting the liquid crystals of the polymer matrix so as to prevent them from escaping from the polymer matrix.

According to another embodiment, the composite is a polymer and liquid crystals gel. This embodiment has the advantage of allowing an easy change in the orientation of the liquid crystals for relatively low pressure voltages compatible with the energy generated by the movement of the eye. In a polymer gel, the movement of the liquid crystals is facilitated. As already mentioned, a polymer protection envelope can also be added.

According to still another embodiment of the invention, the composite is a polymer matrix including a dispersion of liquid crystal droplets. The droplets can be micro-droplets or nano-droplets. This embodiment has the advantage of being able to present an optical diffusion of the lens compatible with the considered applications. This embodiment also has the advantage that the electrical voltage to be applied to cause the orientation of the liquid crystals to change is relatively low and compatible with the energy generated by the movement of the eye.

In such three embodiments, the fact that the liquid crystals are associated with the polymer in the form of a composite has the advantage of allowing a flexibility of the lens which thus makes it possible to fold it to introduce it into the eye in the case of intra-ocular lens, so that the required cut in a patient's eye is relatively small. The shape memory properties of the polymer then enable the lens to go back to its useful shape, which substantially corresponds to a crystalline further to the folding and introduction of the lens.

In addition, according to the invention, the liquid crystals can be either nematic liquid crystals having the advantage of being the most currently known crystals and thus enabling a simple embodiment, or ferroelectric liquid crystals which have the advantage of having a correct electrical response and thus a better reaction to the voltage applied, even though the latter is relatively low, during the movement of the eye.

The polymer associated with the liquid crystals in the lens can be a polyacrylate having an optical index $n_{poly}$ substantially equal to the average optical index of the liquid crystals $n_{CL}$, so as to prevent diffusion phenomena within the lens.

Now, other advantageous characteristics of the transparent electrodes according to the invention will be described according to the particular embodiment of the invention described here-above.

According to one embodiment of such electrodes, these include a mixed indium/tin oxide material known as ITO. This material has the advantage of being a conducting and usually transparent material.

According to one embodiment of such electrodes, these include a conducting polymer. The advantage of such conducting polymers is that they have a good biological compatibility and can thus be easily used more particularly in the case of an intra-ocular device. This conducting polymer also has the advantage of being usable as a protection envelope of the lens associated with the liquid crystals to keep the crystals in the polymer.

In addition, in the embodiments wherein a voltage is applied to the liquid crystals, so as to modify their orientation, it is advantageous that the liquid crystals currently change orientation, for example without a part of the crystals rotating in one direction and the other part rotating in another direction.

This additional advantage is obtained through the characteristics according to which liquid crystals are inclined with respect to an homeotrope orientation in the lens, independently of the application of any voltage. This inclination corresponds to a pre-orientation of the liquid crystals and can be obtained through the application of a pre-orientation of an electrical field during the manufacturing of the lens and more particularly during the polymerisation of the lens.

This preferred orientation can also be obtained through particular chemical treatments of the external surfaces of the lens, for example through the deposition of molecules inducing a specific orientation of the molecules of liquid crystals through weak chemical connections.

In addition, the refraction index of the polymer is substantially equal to the refraction index of the liquid crystals, so as to obtain a transparent medium.

In addition, it is also advantageous that the converter can simply generate a voltage and does not hinder the vision of the user of the device according to the invention when the latter is placed in the user's eye.

This additional advantage is reached according to one embodiment of the invention through the characteristic according to which the converter includes a pair of electrodes transparent in the visible region, the electrodes of the pair of electrodes being positioned on either side of the lens.

So, the electrodes form a capacitor around the lens. The capacitor makes it possible to apply the voltage to the material having a variable refraction index, so as to vary the refraction index during the movement of the eye. The fact that the electrodes are transparent in the visible region further makes it possible not to hinder the vision of the user of the device.

In addition, in order to provide a device whose response to the movement of the eye is satisfactory, so as to correctly modify the optical properties of the lens, the converter may include a pressure sensor and a transducer capable of transforming a pressure into an electrical and/or magnetic and/or electromagnetic signal. Thus, when the eye moves, the pressure generated by such movement is detected by the pressure sensor and the transducer will then generate the electrical and/or magnetic and/or electromagnetic signal. More generally, the converter may include means for detecting the mechanical energy caused by a rotation of one eye or both eyes.

The converter also preferably includes a computer so as to adapt the electrical and/or magnetic and/or electromagnetic signal generated as a function of the detected mechanical energy, and more particularly pressure. The pressure sensors and the computer preferably communicate through ultrasound.

In addition, in the case of an accommodation movement of a user's eyes corresponding to a convergence of the eyes, it is advantageous that the optical properties of the lens are not modified out of the accommodation path, but start from a point called punctum remotum corresponding to the point from which a sound eye starts accommodating. Thus, the accommodating simulation effect gets much closer to a real accommodation. This punctum remotum is situated approximately five meters away from the eyes.

This additional advantage is obtained according to one embodiment of the invention through the characteristic according to which the converter is so arranged that the threshold electrical voltage for the modification of the orientation of the liquid crystals is reached when a movement of accommodation of the eyes starts at the punctum remotum.

As a matter of fact, it is known that for liquid crystals, the effect of the modification of the orientation starts only from a threshold electrical voltage for the modification of the orientation. From this threshold voltage, the crystals start to orientate their dipolar moment. For liquid crystals in a thin film, beyond this threshold voltage, the variation of the orientation of the liquid crystals is then substantially proportional to the applied electrical voltage. This effect is known as a Fréedericksz effect.

Using this threshold voltage effect, the converter is then arranged so that the orientation effect starts only when the movement of the eyes reaches the punctum remotum. This makes it possible to obtain a good simulation of the accommodation during the movement of accommodation of the eyes corresponding to a convergence. This advantage is more particularly reached because the electrical and/or magnetic and/or electromagnetic signal generated results from the mechanical energy due to the convergence of the eyes, which makes it possible to adapt the signal as a function of this movement.

On an average, the punctum remotum is located approximately five meters away from the eyes. Thus, the converter can be so arranged that the threshold voltage for the modification of the orientation of the liquid crystals is reached when the optical axes of both eyes intersect at a distance of approximately five meters with respect to the eyes.

This particular arrangement of the converter can be obtained by programming the above-mentioned computer so as to reach this result. This result is also reached through the appropriate selection of materials, more particularly for the soft lens.

The invention also relates to a soft lens including a polymer material in which a material having a refraction index likely to vary under the action of an electrical and/or magnetic and/or electromagnetic signal liable to be produced through the transformation of the mechanical energy produced during the movement of an eye, is included.

All the characteristics described here-above as relating to the lens in the device for the vision correction are also applied to such a lens.

Now, an embodiment of the invention will be described while referring to the appended drawings wherein.

Figure 1:
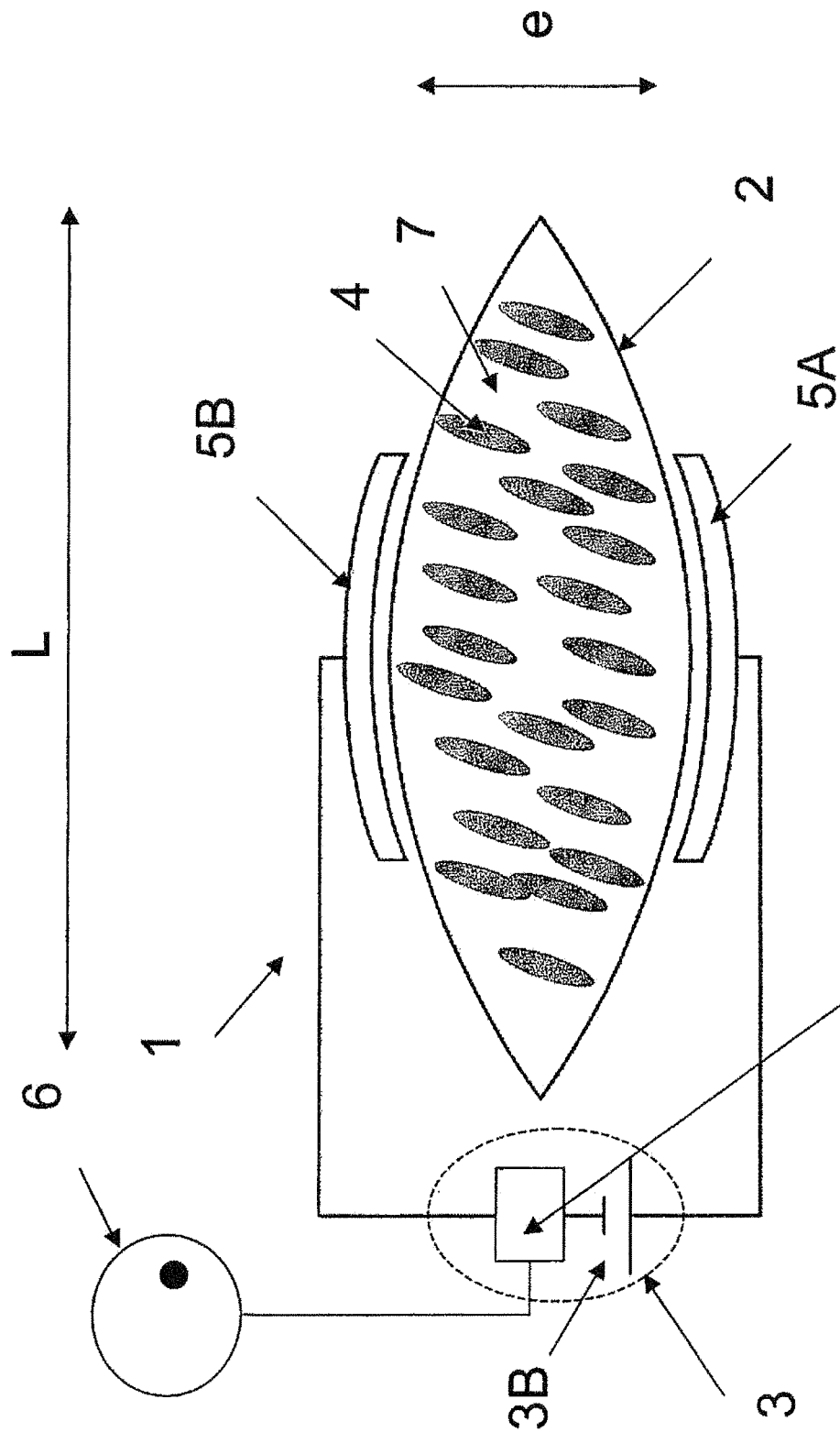
FIG. 1 shows a device for the vision correction of an eye according to one embodiment of the invention.

In FIG. 1, a device 1 for the vision correction of an eye 6 includes a lens 2. The lens 2 includes liquid crystals 4 in a polymer 7. The lens 2 is surrounded on both sides by transparent electrodes 5A and 5B. The muscle tissues of the eye 6 are connected to a converter 3 including means 3A for detecting the movement of the eye 6 and means 3B for generating an electrical signal as a response to such movement of the eye. The means 3A for example include pressure sensors.

The converter 3 including the means 3A for detecting a movement of the eye 6 and generating an electrical signal as a response to this movement can be as described in the international application WO 2004/004605. In particular, as described in this document, the converters 3 may include one or several strain gages which can be made from miniature absolute pressure sensors 3A, which are inserted under the insertion tendon of the external rectus muscles. This can be millimetric microstructures on silicon, which are supplied without any contact and without any battery, like through induction. Such systems include a sensitive element, a converter and a coupler associated to a secondary antenna enabling the remote supply of the system and the remote transmission of the pressure measurement.

More precisely, the sensitive element is a mechanical microstructure which is deformed under the effect of a force, i.e. the pressure it is submitted to, a deformation which causes the modification of capacities integrated in the sensitive assembly. The electrical value of the variations in capacities is transformed into a digital signal through the converter. The sensitive element may also show shape variations or axial deformations such as extensions or compressions.

Thanks to the converter 3 as described here-above, it is thus possible to obtain, in response to a movement of the eye, an electrical signal corresponding to the voltage between the transparent electrodes 5A and 5B of approximately 1, to 5, volts. The generated electrical tension depends on the movement of the eye, such movement being the movement of an eye or a combined movement of both eyes. In the example described, the converter 3 is a transducer which transforms the mechanical energy caused by the movement of an eye into an electrical signal. Other embodiments of this converter can be considered, so long as an electrical and/magnetic and/or electromagnetic signal is generated in response to a movement of the eye.

Now, the lens 2 and the liquid crystals 4 associated within the scope of an accommodation corresponding to a convergence of the eyes will now be described in greater details.

The lens 2 is a symmetrical biconvex lens having a convergence C close to 21 dioptres for 1 emmetrope eye, with an average refraction index n equal to 1.5 and a radius of curvature R. For a biconvex lens 2, it is known that the convergence is given by the relation C=2(n−1)/R, so that the curvature is in this case 5 centimeters. The diameter of the lens 2 is L=6 millimeters, and the radius of curvature is 50 millimeters. The thickness of the lens of the order of 180 micrometers can be deduced therefrom.

In this case, if it is desired that the convergence varies by approximately 3 dioptres during the adjustment of the lens, we have ΔC=(2.Δ)/R=3 dioptres, i.e. Δn=0.0075.

According to this example, the liquid crystals must thus be capable of modifying the refraction index having a value equal to Δn=0.0075,, which is possible, since if $n_e$ and $n_o$ are respectively the extraordinary and ordinary indexes of the liquid crystals we have:

$$0.05 < n_e - n_o - \Delta n < 0.25$$

According to the invention, the liquid crystals have ordinary and extraordinary indexes which are respectively equal to 1.5 and 1.65.

According to the orientation of the liquid crystal molecules in the lens, it is known that the apparent index of the medium comprising the liquid crystal varies.

For a planar orientation wherein the molecules are parallel to the lower and upper substrates composing the internal surface of the lens, for a natural and non-polarised light, it is known that the apparent index is equal to:

$$N_p = [(n_o^2 + n_e^2)/3]^{1/2} = 1.5767$$

Figure 2:
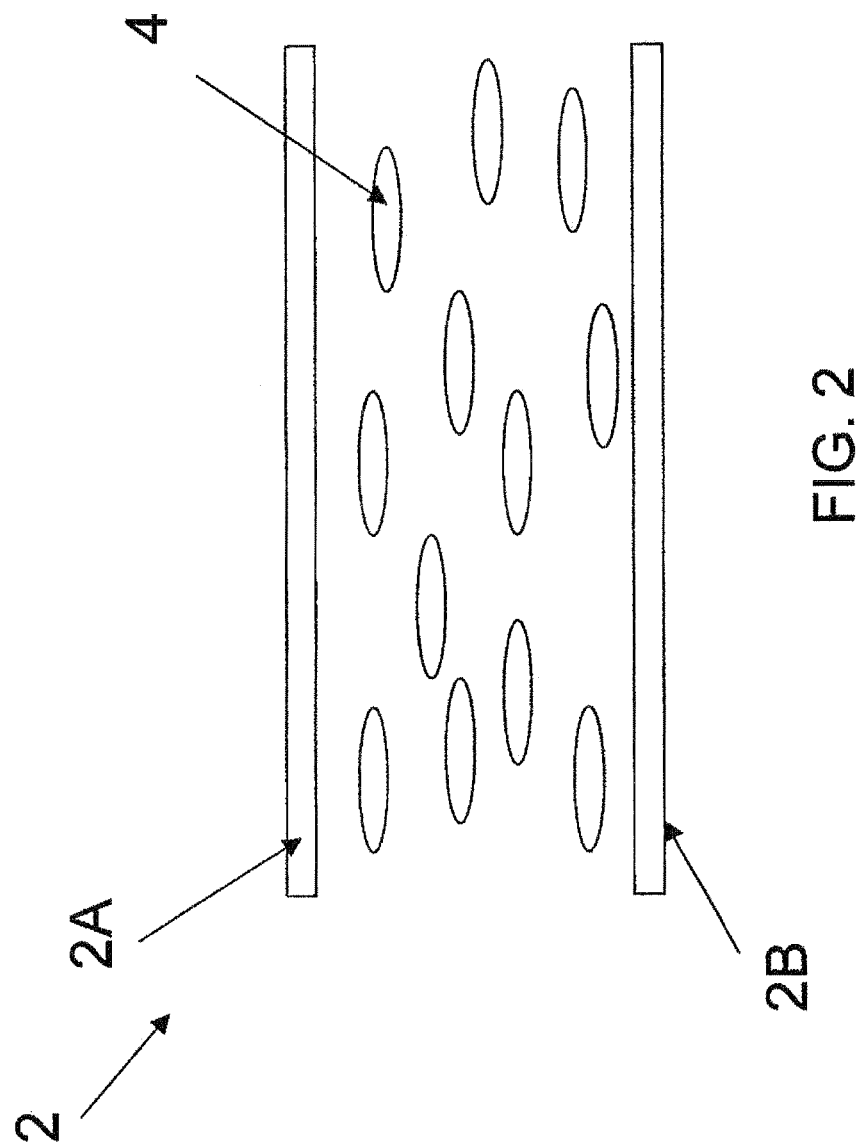
FIG. 2 shows a planar orientation of the liquid crystals in the lens according to the invention.

This planar orientation is schematically represented in FIG. 2. The liquid crystals 4 are positioned parallel to the surfaces 2A and 2B of the lens 2.

For an homeotropic orientation wherein the molecules are perpendicular to the lower and upper substrates composing the internal surface of the lens, for a natural and non-polarised light, it is known that the apparent index is equal to:

$$n_p = n_o = 1.65$$

Figure 3:
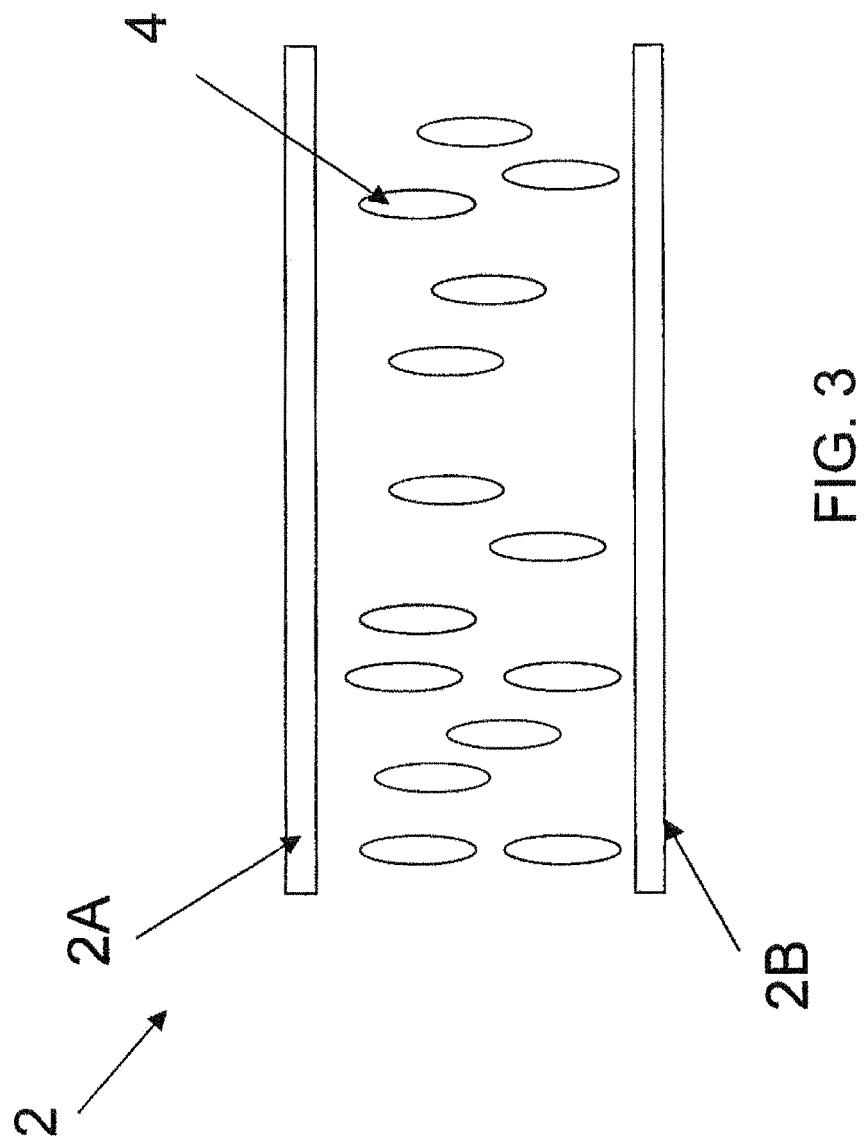
FIG. 3 shows a homeotrope orientation of the liquid crystals in the lens according to the invention.

This homeotropic orientation is schematically represented in FIG. 3. The liquid crystals 4 are positioned perpendicularly to the surfaces 2A and 2B of the lens 2.

During a change in the orientation of the liquid crystals under the effect of a voltage during a movement of the eye, the liquid crystals can change from a homeotropic orientation to a planar orientation.

In this case, the maximum variation of the index is $n_p - n_o = 0.0767$ which is thus perfectly acceptable to perform a change in convergence by 3 dioptres, as mentioned above.

More precisely, according to one embodiment of the invention, it is desired for the device according to the invention to make it possible to increase the convergence, with a constant radius of curvature, by switching from a far vision to a near vision. The arrangement of the liquid crystals in the lens is then adapted to reach this result.

For this purpose, it is necessary for the lens 2 to have a low index for a far vision, thus for the liquid crystal molecules to have a homeotropic orientation and a high index for a near vision, thus for the liquid crystal molecules to have a planar orientation since, as mentioned above, $n_p$ is greater than $n_o$.

In addition, the dielectric anisotropy of the liquid crystal molecules for two orthogonal positions of an electrical field as Δε, with:

Δε>0 if the dipolar moment is directed along the main direction of the extension of molecules;

Δε<0 if the dipolar moment is orientated perpendicularly to the main direction of the molecules extension.

To have a positive variation of the index through the switching of the molecules to a planar orientation under the effect of an electrical field, a liquid crystal with a negative dielectric anisotropy and a homeotropic orientation is selected in the absence of a field. The converter 3 is then arranged so that the eye is at rest in a far vision and that no electrical field is supplied to the liquid crystal in a far vision.

In order to have a positive variation of the index through the switching of the molecules to a homeotropic orientation under the effect of an electrical field, a liquid crystal with a positive dielectric anisotropy and a planar orientation is selected in the absence of a field.

In order to guarantee that the orientation of the liquid crystal molecules is homeotropic on the whole thickness of the liquid crystal, the surfaces limiting the lens in a way known per se are treated, for example in the field of liquid crystal display devices.

A pre-orientation of the liquid crystals can thus be obtained by applying an electrical pre-orientation field during the manufacturing of the lens and more particularly during the polymerisation of the lens.

The same surface treatment procedures and the application of an electrical pre-orientation field are applicable to guarantee a planar orientation of the molecules on the whole thickness of the lens.

The effect of the voltage applied to the liquid crystals is then an orientation of the dipolar moment of the liquid crystals perpendicularly to the surfaces limiting the liquid crystals. To obtain a homogenous orientation in the presence of the electrical field, a pre-orientation is imparted to the molecules in the absence of a field. The liquid crystals are thus slightly inclined with respect to the homeotropic position.

The liquid crystals used can be nematic liquid crystals, or ferroelectric liquid crystals. Depending on the type of liquid crystals selected, the conditions of the orientation may vary more particularly as a function of the dielectric anisotropy Δε.

Figure 4:
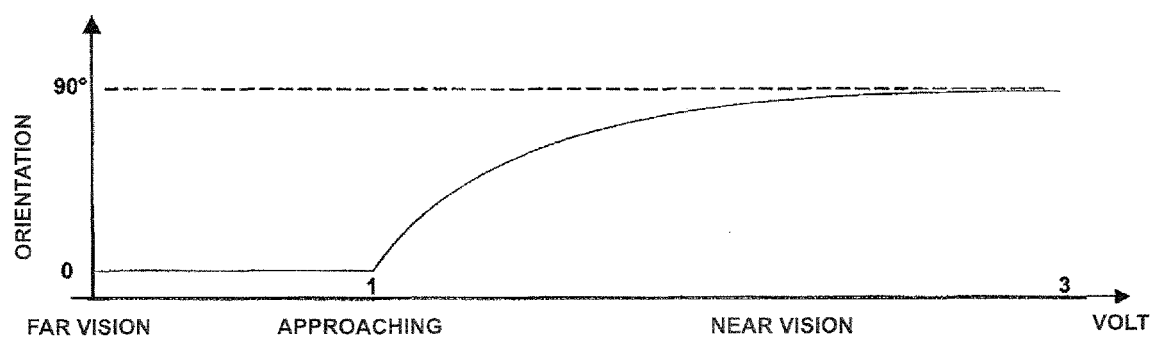
FIG. 4 is a curve showing the variation in the orientation of the liquid crystals as a function of the voltage to the lens according to the invention.

Now the curve of the response of the liquid crystals as a function of the voltage applied in the lens in now described while referring to FIG. 4. This curve is known per se within the scope of the Fréedericks effect. The threshold of $V_o$ is given by the following expression for a thin film corresponding to the thickness of the lens:

$V_o = \Pi(K/\Delta\epsilon)$ with K being the elasticity constant of the liquid crystal.

Beyond this threshold voltage, the angle α giving the alignment orientation of the liquid crystals molecules with the surface of the lens 2 is proportional to the electrical field applied, still with a thin film.

As the thickness of the lens is approximately 180 micrometers, the thin film condition is satisfied.

For a conventional liquid crystal, the preceding formula gives a threshold voltage of approximately 1 volt and a maximum voltage to obtain a planar orientation of the order of 3 volts.

These voltages are compatible with the electrical energy which can be generated by the converter 3 further to the movement of the eye or the eyes.

Thus, during the approaching between the far vision and the near vision, the index of the lens is not modified. This characteristic corresponds to the situation for a sound crystalline which makes no accommodation before the convergence point of the eyes reaches the distance of approximately 5 meters. This point of the starting of the accommodation is called punctum remotum.

The converter is then arranged so that, when the eyes reach such a 5 meter convergence, the electrical signal generated by the converter corresponds to the voltage equal to the threshold voltage $V_o$. The modification of the orientation is then linear when the eyes converge further.

An exemplary embodiment of the lens 2 associated with the liquid crystals 4 will now be described in greater details.

Generally, the lens 2 includes a composite of a polymer material 7 and liquid crystals 4. Thanks to this composite, the lens can be easily handled without irreversibly modifying the molecular arrangement of the liquid crystals which would make the device unserviceable.

This lens 2 is for example a polymer matrix 7 having a biconvex shape formed by liquid crystal 4. A protection envelope also made of polymer possibly protects this polymer matrix. The polymer used is a polyacrylate having an optical index $n_{poly}$ which is substantially equal to the average optical index of the liquid crystals $n_{CL}$ so as to prevent diffusion phenomena within the lens.

According to a first alternative solution, the lens 2 also includes a polymer 7 and liquid crystal gel 4. The liquid crystals 4 are then frozen in the polymer network while being easily movable under the action of the electrical field.

According to a second alternative solution, the lens 2 can also include droplets of liquid crystals 4 in a polymer matrix 7. In this case, the liquid crystals 4 are preferably of a ferroelectric type. The insertion of polymer droplets in a polymer matrix is known per se. The manufacturing method of such a structure is for example disclosed in the work by [M. BOUSSOUALEM (doctoral thesis of Université du Littoral Côte d'Opale December 2005) "Contribution à l'optimisation de la qualité de regulation lumineuse de films composites: etude physicochimique aux interfaces matrice-phase complexe"; M. BOUSSOUALEN, M. ISMAILI, J.-F. LAMONOER, J. M. BUISINE, F. ROUSSEL Polarization field-effect at liquid Crystal droplets-polymer interface Physical Review 73 (2006)].

In all these embodiments, the liquid crystals 4 are included in a polymer material 7, so as to have a good reactivity to the electrical field, while being relatively stable in the absence of an electrical field.

In all these embodiments and more particularly when the lens is used as an intra-ocular implant, it can include an optical part from where arms also called haptic arms protrude, which are used for fixing the implant in the patient's eye.

Now, the electrodes 5A and 5B will be described in greater details. Such electrodes 5A and 5B are transparent electrodes made of a mixed indium/tin oxide material. They are positioned so as to follow the shape of the surfaces of the lens 2 and are thus concave. They are positioned in relation to the lens 2 so as to apply a voltage in the area of the lens 2 which includes the liquid crystals.

According to an alternative solution, such electrodes 5A and 5B include a conducting polymer.

Now, the device 1 according to the invention will be described in operation.

Further to surgery, the lens 2 is positioned in the eye for example as an intra-ocular implant, in the case of cataract surgery. The converter 3 is connected to the muscles of the eye to detect a movement of the eye and generate an electrical signal in response. This electrical signal can be supplied to the lens 2, as a voltage, through the electrodes 5A and 5B.

When the bearer of the device 1 has a movement of the eye for example a convergence movement of both eyes corresponding to the switching from a far vision to a near vision, the converter 3 detects this movement through the sensor 3A. When this movement is detected, an electrical signal is generated by the generation means 3B. This electrical signal is supplied to the electrodes 5A and 5B so that a voltage is generated between the electrodes 5A and 5B.

According to the value of this voltage and depending on the graph of the response, as illustrated in FIG. 4, the orientation of the liquid crystals 4 is modified. As previously described, these liquid crystals can be selected so that the apparent index of the lens 2 increases in the case of convergence of the user's eyes.

When the index has increased, the user has a correct near vision, which does not require lenses.

Now, alternative solutions to the invention will be described.

The fact that the electrical signal is supplied to the lens as a voltage so as to modify the orientation of the liquid crystals has been described. However, it is also possible that the liquid crystals are orientated under the effect of the magnetic field which will then entail a modification of the refraction index of the lens, as mentioned above. This effect, which is similar to the above-mentioned Fréedericks effect, is known. To generate the magnetic field, electromagnetic transducers can be used on the muscles of the eye and apply a magnetic field generated by the movement of the eye to the lens. This embodiment has the advantage of not requiring electrodes at the lens.

Figure 5:
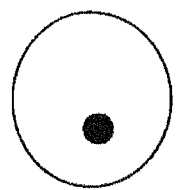
FIG. 5 shows four situations of a user's eyes which can activate or not the generation of an electrical signal, further to the detection of the movement of the eyes.
Figure 5:
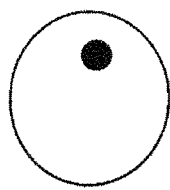
Figure 5:
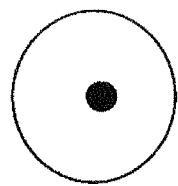
Figure 5:
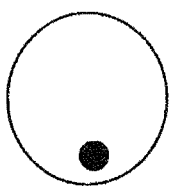
Figure 5:
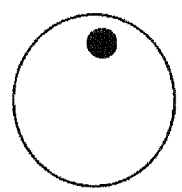

In addition, the device has been described within the scope of a particular movement of the eyes corresponding to the switching of a far vision to a near vision. It should be noted that the converter can detect any movement of one eye or both eyes and generate the electrical signal as a function of this movement. While referring to FIG. 5, the converter can be arranged so that the electrical signal is for example generated in the case "d" for both eyes, in the cases "b and c" for the eye in convergence alone and for none of the eyes in the case "a".

In addition, an embodiment in which the lens 2 is used as an intra-ocular implant has been described. As an alternative solution, the lens 2 can also be a contact lens or an ocular glass. In the latter case, it is sufficient to connect the ocular glass to the muscles of the eye or of both eyes and to detect the movement of the eye or of the eyes using the converter. Thanks to the converter according to the invention, the movement of the eyes can then be converted into an electrical signal which can modify the optical index of the ocular glass.

The invention claimed is:

1. A device for the vision correction of an eye including:
   a converter generating an electrical and/or magnetic and/or electromagnetic signal solely from mechanical energy generated by a movement by the eye;
   a soft lens intended to be aligned with the eye,
   the converter being positioned in relation to the lens such that the electrical and/or the magnetic and/or the electromagnetic signal generated during the movement of the eye cause the optical properties of the lens to change,
   wherein the lens includes a polymer material containing a material having a refractive index that can vary under the action of the electrical and/or magnetic and/or electromagnetic signal generated solely from the converter.

2. A device according to claim 1, wherein the material includes liquid crystals having an orientation liable to vary under the action of the voltage of the electrical and/or magnetic and/or electromagnetic signal during the movement of the eye.

3. A device according to claim 2, wherein the converter is arranged such that the threshold effect of the modification of the orientation of the liquid crystals is reached when an accommodation movement of the eyes starts at the punctum remotum.

4. A device according to claim 2, wherein the converter is arranged such that the threshold effect of the modification of the orientation of the liquid crystals is reached when the optical axes of both eyes intersect at a distance of approximately five meters in relation to the eyes.

5. A device according to claim 2 wherein the converter includes a pair of electrodes which are transparent in the visible region, with the electrodes of the pair of electrodes being positioned on either side of the lens.

6. A device according to claim 5, wherein the electrodes of the pair of electrodes include a mixed indium/tin oxide material.

7. A device according to claim 5, wherein the electrodes of the pair of electrodes include a conducting polymer material.

8. A device according to claim 2 wherein the converter includes a pressure sensor, a transducer able to transform a pressure resulting from the movement of the eye into an electrical and/or magnetic and/or electromagnetic signal.

9. A device according to claim 1 or 2, wherein the lens includes a composite of the polymer material and liquid crystals.

10. A device according to claim 9, wherein the composite is a polymer matrix swollen with liquid crystals.

11. A device according to claim 9, wherein the composite is a polymer and liquid crystals gel.

12. A device according to claim 11, wherein the polymer is a polyacrylate having an optical index substantially equal to the average optical index of the liquid crystals.

13. A device according to claim 9, wherein the composite is a polymer matrix including a dispersion of liquid crystal droplets.

14. A device according to claim 9, wherein the liquid crystal are nematic liquid crystals.

15. A device according to claim 9, wherein the liquid crystals are ferroelectric liquid crystals.

16. A device according to claim 9, wherein the liquid crystals have a negative dielectric anisotropy and a homeotropic orientation in the absence of an electrical field.

17. A device according to claim 9, wherein the liquid crystals have a positive dielectric anisotropy and have a planar orientation in the absence of an electrical field.

18. A device according to claim 9, wherein the liquid crystals are inclined in relation to an homeotrope orientation in the absence of an electromagnetic field.

19. A device according to claim 9, wherein the liquid crystals have an orientation liable to vary under the action of the voltage of the electrical and/or magnetic and/or electromagnetic signal during the convergence movement of both eyes.

* * * * *